(12) United States Patent
van den Broek et al.

(10) Patent No.: US 10,448,882 B2
(45) Date of Patent: Oct. 22, 2019

(54) DETERMINING A SEDENTARY STATE OF A SUBJECT

(71) Applicant: KONINKLIJKE PHILIPS N.V., Eindhoven (NL)

(72) Inventors: Chantal Nathalie van den Broek, Veldhoven (NL); Paul Marcel Carl Lemmens, Eindhoven (NL); Louisa Simone Ruijs, Eindhoven (NL); Francesco Sartor, Eindhoven (NL); Erik Gosuinus Petrus Schuijers, Breda (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 174 days.

(21) Appl. No.: 15/273,980

(22) Filed: Sep. 23, 2016

(65) Prior Publication Data
US 2017/0079578 A1 Mar. 23, 2017

(30) Foreign Application Priority Data
Sep. 23, 2015 (EP) .................................... 15186396

(51) Int. Cl.
*A61B 5/02* (2006.01)
*A61B 5/00* (2006.01)
(Continued)

(52) U.S. Cl.
CPC .......... *A61B 5/4561* (2013.01); *A61B 5/0205* (2013.01); *A61B 5/6801* (2013.01);
(Continued)

(58) Field of Classification Search
CPC ... A61B 5/4561; A61B 5/0205; A61B 5/6801; A61B 5/1118; A61B 2562/0219;
(Continued)

(56) References Cited

U.S. PATENT DOCUMENTS

2002/0170193 A1 11/2002 Townsend et al.
2007/0142868 A1 6/2007 Moon et al.
(Continued)

OTHER PUBLICATIONS

Altini, et al., "Combining Wearable Accelerometer and Physiological Data for Activity and Energy Expenditure Estimation", Wireless Health 13, Nov. 1-3, 2013.
(Continued)

*Primary Examiner* — Rex R Holmes (57) ABSTRACT

Various embodiments relate to methods, devices, and systems for ascertaining a sedentary body posture of a subject including: determining if the subject is in a sedentary state when the subject is sedentary for a pre-determined time; receiving a heart rate signal for least one heart rate feature when the subject is in the sedentary state; deriving at least one heart rate feature value when the subject is in the sedentary state further including filtering an arousal value from the received heart rate signal, so as to reduce an influence of the arousal on the determination of the sedentary posture; and determining the sedentary body posture of the subject based on a comparison between the derived at least one heart rate feature value and a pre-determined range associated with the corresponding at least one heart rate feature, wherein for each sedentary body posture, a pre-determined range is stored.

14 Claims, 8 Drawing Sheets

(51) Int. Cl.
*A61B 5/0205* (2006.01)
*G06F 19/00* (2018.01)
*A61B 5/11* (2006.01)
*A61B 5/024* (2006.01)
*A61B 5/053* (2006.01)

(52) U.S. Cl.
CPC ...... *G06F 19/3418* (2013.01); *G06F 19/3481* (2013.01); *A61B 5/024* (2013.01); *A61B 5/0533* (2013.01); *A61B 5/1116* (2013.01); *A61B 5/1118* (2013.01); *A61B 2560/0223* (2013.01); *A61B 2562/0219* (2013.01)

(58) Field of Classification Search
CPC ..... A61B 5/0533; A61B 5/1116; A61B 5/024; A61B 2560/0223; G06F 19/3418; G06F 19/3481
See application file for complete search history.

(56) References Cited

U.S. PATENT DOCUMENTS

2009/0322540 A1 12/2009 Richardson et al.
2013/0132028 A1 5/2013 Crankson et al.
2014/0278220 A1 9/2014 Yuen

OTHER PUBLICATIONS

Doccheck Medical Services Gmbh: "Schellong-Test", DocCheck Flexikon, Jan. 20, 2015, retrieved from the internet: URL:https://web.archive.org/web/20150120120128/http://flexikon.doccheck.com/de/Schellong-Test (Abstract).
Anonymous: "Orthostase-Reaktion", Wikipedia, Jul. 18, 2013, XP055323239, retrieved from the Internet: URL:https://de.wikipedia.org/w/index.php?title=Orthostate-Reaktion&oldid=120655309 (Abstract).

DETERMINING A SEDENTARY STATE OF A SUBJECT

TECHNICAL FIELD

Various embodiments relate to activity tracking and more particularly, but not exclusively, to a method, a device, and a system for determining a sedentary state of a subject.

BACKGROUND

In the field of healthcare, fitness and leisure activities, the use of activity trackers or activity monitors for monitoring a physical activity of a subject has become more and more popular. Starting from pedometers, which count the number of steps, the technology has evolved towards more sophisticated activity trackers which distinguish between different types of physical activities such as walking, running or cycling. For example, walking and running can be distinguished from being sedentary based on a step frequency. Exemplary systems feature for example a wrist band with a sensor, wherein the wristband is in communication with a smart phone that is running a fitness tracking app.

SUMMARY

While existing activity trackers successfully distinguish between different types of activities, such as walking and running, they do not distinguish between different sedentary states, such as standing, sitting and lying. Static sedentary body postures, such as standing, sitting and lying, are hard to distinguish by means of unobtrusive wearable devices such as motion sensors. For instance, the current activity trackers using motion sensors only determine if the subject is sedentary, however, these trackers do not provide further information if the person is sedentarily standing, sitting or lying.

Knowing whether a subject is sedentarily standing/sitting/lying can be very relevant information in many instances. For example, pregnant women are at high risk of lower limbs edema and of developing varicose veins when standing still. In some occupations standing still is a common postural behavior, for example for hairdressers or production workers, which increases the risk for those workers of problems to the lower limbs. Similarly sedentarily siting for a longer period of time might not be helpful for employees who have desk/office jobs Accordingly, various embodiments described herein provide an alternative method and a device for determining a sedentary state of a subject which does not require evaluating signals from multiple sensors at different locations of the user's body to detect the individual positions of each body part.

Various embodiments described herein relate to a method for determining a sedentary state of a subject is presented that include: determining if the subject is in a sedentary state, wherein the subject is determined to be in the sedentary state when the subject is being sedentary for at least a pre-determined time threshold; receiving a heart rate signal indicative of at least one heart rate feature of the subject; deriving, from the obtained heart rate signal, at least one heart rate feature value corresponding to at least one heart rate feature, when the subject is determined to be in the sedentary state, wherein deriving the heart rate feature value further includes filtering (S7) an arousal value from the received heart rate signal, so as to reduce an influence of the arousal on the determination of the sedentary posture; and determining the sedentary body posture of the subject based on a comparison between the derived at least one heart rate feature value and a pre-determined range associated with the corresponding at least one heart rate feature, wherein for each sedentary body posture a pre-determined range corresponding to the at least one heart feature is stored.

Various embodiments are partly based on the insight that different sedentary body postures can be reliable distinguished on the basis of heart rate features, such as heart rate, heart rate variability, etc. Thus, recognizing range of these heart rate features corresponding to each sedentary body posture and using it to identify different sedentary body postures by receiving real-time information from the heart rate feature signal enables distinguishing different sedentary body postures.

In a further embodiment, the pre-determined time threshold is selected based on recovery time associated with subject-specific characteristics, such as, male, young, fit, etc. The recovery time can be thus selected from standard population data. In a yet further embodiment, the pre-determined time threshold can be personalized to the subject based on his/her personal recovery time, in other words, his/her resting heart rate.

In an embodiment, filtering the arousal value further includes a. receiving Inter-Beat-Intervals (IBIs) for a pre-defined recording time, wherein the Inter-Beat-Intervals being a heart rate feature; b. plotting a frequency distribution of the IBIs gathered in the pre-defined recording time; and c. comparing the plotted frequency distribution in the pre-defined recording time with a template frequency distribution associated with IBIs for different sedentary body postures.

In an embodiment, the comparison between the two frequency distributions further includes comparing the mean IBIs associated with each of the frequency distributions, wherein the comparison of the mean IBIs determines the sedentary body posture.

In a further embodiment, filtering the arousal value further includes calculating a heart rate ($HR_{Arousal}$) indicative of arousal based on Galvanic Skin Response (GSR) signal and removing the calculated heart rate ($HR_{Arousal}$) indicative of arousal from the overall heart rate ($HR_{Total}$) received from the heart rate signal to derive the heart rate ($HR_{Sedentary}$) indicative of the sedentary body posture, wherein the heart rate is a heart rate feature.

The arousal value is indicative of the arousal component present in the derived heart rate feature value. Various examples of the arousal component may include but are not limited to cognitive load, tension, stress induced by loud noise, perceived danger, excitement, joy, etc. One can imagine that in the moments of arousal the heart rate gets elevated. Thus, it is very important that the method determines if the heart signal indicative of the heart rate feature value includes any influence because of arousal. If such a determination of arousal component is not present, then there are high chances that the body posture will be misclassified/incorrectly determined. In some embodiments, the arousal value corresponding to arousal component in the heart rate signal is measured based on the heart rate feature information. In another embodiment, the arousal component in the heart signal is measured based on skin conductance. In an embodiment, the sedentary body posture is one of sedentarily standing, sedentarily sitting and sedentarily lying. In other words, these are different types of sedentary body postures.

The method has numerous advantages. The method helps the user to understand if he is in a particular sedentary body posture. It helps the user to timely take actions in order to avoid being in the sedentary posture for a longer period of time. For instance, if the person is constantly sitting for a long time then a method as described above gives him information about his sedentary state so that he can take an action, such as a coffee break, to move out the sedentary state.

In various embodiments, the heart rate feature is at least one of a group including a heart rate (beats per minute) and a heart rate variability feature. Various examples of heart rate variability features include but are not limited to
 a mean inter beat interval of the heart rate;
 a standard deviation of the mean inter beat interval;
 a low frequency power parameter indicative of a power in the spectral band between 0.04 and 0.15 Hz;
 a high frequency power parameter indicative of a power in the spectral band between 0.15 and 0.4 Hz;
 a mean of absolute successive inter beat intervals differences;
 a root-mean-square of successive inter beat intervals differences;
 a percentage of successive inter beat interval differences larger than 50 ms;
 a standard deviation of successive inter beat interval differences;
 a phase of the high frequency pole;
 a sample entropy; and
 a Teager-Kaiser energy.

In a further embodiment, determining if the subject is sedentary further includes checking if the motion information corresponding to the subject is below a pre-determined motion threshold. For instance, the motion information from the user may indicate that the person is not moving, however, it is important to understand if the person is truly sedentary. Thus, only if the motion information is below a pre-determined motion threshold it is determined that the person is sedentary. The motion information may be further recorded for a pre-defined time interval/a pre-determined time threshold, for instance 2 minutes. Thus in combination if the motion information is below the pre-determined motion threshold for the pre-determined time interval, the user can be ascertained to be sedentary.

In yet another embodiment, the pre-defined time interval can be further set by the subject based on his work profile.

In a further embodiment, the pre-determined range of at least one derived heart rate feature corresponding to each sedentary body posture is stored in at least one of a table and/or in form of a Gaussian distribution. As described above, the at least one derived heart rate feature value is compared with the stored ranges to determine the sedentary body posture. One of the ways is to store the ranges associated with each sedentary body posture is in form of a lookup table. Inventors have realized that in each sedentary body posture, the human heart behaves in a particular fashion. For instance, when the user is sedentarily standing, the heart rate, or the mean heart rate, of the user is typically greater than 73 bpm (beats per minute). Similarly, for sedentarily sitting (62-73 bpm) and for sedentarily lying less than 62 bpm is observed. The corresponding ranges are stored in the look up table. Thus in practice, once the subject is determined to be in a sedentary state; his heart rate feature value(s) is derived. For instance, mean of heart rate can be calculated for a pre-defined recording time, such as 20 seconds, after the person was determined to be sedentary. The mean heart rate can be then looked up in the table to determine the corresponding sedentary body posture accordingly. In an embodiment, the coefficient of variation of heart rate feature values (in this case for mean heart rate value) for these 20 seconds is set to be less than 20%.

In another embodiment, the heart rate feature value can be derived for the pre-defined time interval in which subject was determined to be sedentary. In other words, the heart rate feature value need not be determined after the user was ascertained to be sedentary but in the pre-defined interval itself in which he was determined to be sedentary. In yet another embodiment, the heart rate feature value can be derived for the pre-defined time interval in which the subject was determined to be in the sedentary state and the pre-defined recording time after the user was ascertained to be in the sedentary state.

In a further embodiment, another way to store the ranges is in form of a Gaussian frequency distribution of heart rate/heart rate variability feature, such as Inter-beat Intervals. For instance, a template frequency distribution, also may be referred to as a baseline distribution, of inter beat intervals (IBIs) can be stored for a particular sedentary body posture. In practice, once it is determined that the user is sedentary, the inter-beat intervals are recorded and a frequency distribution of the inter bear intervals is plotted. Thereafter the sedentary posture is determined based on the comparison between plotted distribution and the stored template distribution. A yet another way is also to determine mean of the template distribution which can be used as the baseline to compare the mean IBI from the plotted distribution. The mean IBIs can be further stored for each of the sedentary body postures in form a lookup table.

In a further embodiment, the method calibrates the pre-determined range corresponding to the at least one heart rate feature for each of the sedentary posture. This is in particular advantageous as a standard look up table or Gaussian distribution for a human may vary from subject to subject. In an embodiment, the method can start with a look up table and/or Gaussian distribution as pre-stored information and then calibrate/personalize the ranges for each sedentary posture corresponding to the user. For instance, in a calibration phase, the user can be prompted to verify if the identified sedentary posture is indeed the body posture he is in currently. If not, then the new range information for the corresponding body posture can be stored accordingly. Another way to personalize is to provide one or more instructions to the subject in order to bring the subject in a sedentary body posture and subsequently record/store a new range corresponding to the at least one heart rate feature associated with the sedentary body posture. The new range can be thereafter used as the pre-determined range for ascertaining the sedentary body posture of the user. The instructions can be provided to the subject in form of voice commands, graphical user interface, etc.

In a further embodiment, the method further includes alerting the subject if the subject is determined to be in the sedentary posture for a time period greater than a pre-defined sedentary time threshold. This is in particular beneficial to the user as he can then move out of the posture in order to avoid various health hazards. For instance, if a sedentary employee is regularly informed about his behavior, he might start to break the behavior by taking regular walks and thus improving his overall health.

In some embodiments, the method described above is computer implemented.

Various embodiments described herein relate to a device for ascertaining a sedentary body posture of a subject. The device includes a sedentary state determination unit configured to check if the subject is in a sedentary state, wherein the subject is determined to be in the sedentary state when the subject is being sedentary for at least a pre-determined time threshold; an input unit for obtaining a heart rate signal indicative of at least one heart rate feature of the subject; a heart rate feature unit for deriving, from the obtained heart rate signal, at least one heart rate feature value corresponding to at least one heart rate feature, when the subject is in the sedentary state, wherein the heart rate feature unit further including an arousal determination unit for filtering an arousal value from the received heart rate signal, so as to reduce an influence of the arousal on the determination of the sedentary posture; a storage unit for storing pre-determined ranges of the heart rate feature values for each of a plurality of the sedentary body postures; and a sedentary body posture determination unit for determining the sedentary body posture of the subject based on comparison between the at least one derived heart rate feature value and the stored ranges.

In a further embodiment, the device further includes a calibration unit for calibrating the pre-determined range corresponding to the at least one heart rate feature for each of the sedentary. In various embodiments, the calibration unit is further arranged for providing one or more instructions to the subject in order to bring the subject in a sedentary body posture; recording a new range corresponding to the heart rate feature associated with the sedentary body posture; and storing the recorded new range as the pre-determined range corresponding to the at least one heart rate feature associated with the sedentary body posture in the storage unit.

In a further embodiment, the device further includes an alert unit to alert the subject if the subject is determined to be in the sedentary posture for a time period greater than a pre-defined sedentary time threshold. Various examples of the alert signal include but are not limited to an audible signal, a visual signal, a tactile signal or any combination thereof. For example, assuming that the apparatus is implemented by a smart phone and/or a wearable device, such as a wrist watch, a sound can be emitted as an audible signal, a message can be displayed on a display screen as a visual signal and/or a vibration can be effected as a tactile signal.

Various embodiments described herein relate to a system including an accelerometer for providing motion information of the subject; a heart rate sensor for receiving a heart signal indicative of at least one heart rate feature of the subject; a device for determining the sedentary body posture of the subject; whereby the device configured to check if the subject is in a sedentary state on the basis of the motion information provided by the accelerometer and the heart rate signal provided by the heart rate sensor, and an output interface for outputting the determined sedentary body posture.

The system as presented above may further include a housing for housing the accelerometer and heart rate sensor, the device and the output interface; and a holding element for holding the housing at body part of the subject. Various examples of such a system include but are not limited to a wearable device, such as a wrist worn device, ankle worn device, etc. and a mobile device along with a strap to conform to at least one body part, such as upper arm, of the subject. The accelerometer may be worn by the subject at different wearing positions, such as neck, pocket, thigh and wrist. In some embodiments, the whole system, including not only the accelerometer but also the device and an output interface (e.g. a display) is worn by the subject. In other embodiments the accelerometer signals may be transmitted to the device in any suitable way, e.g. in a wired or wireless manner, which may be effected on the fly (i.e. in real time during the activity) or later (i.e. in non-real time after the activity). The device may e.g. be an application running on a smart device, such as a smartphone, tablet, smart watch, fitness device, lifestyle device or computer.

In some embodiments described herein, there are provided a computer program which includes program code means for causing a computer to perform the steps of the method disclosed herein when said computer program is carried out on a computer, as well as a non-transitory computer-readable recording medium that stores therein a computer program product, which, when executed by a processor, causes the method disclosed herein to be performed.

It shall be understood that the claimed device and system have similar and/or identical embodiments as the claimed method for determining a sedentary state of a subject.

These and other aspects will be apparent from and elucidated with reference to the embodiments described hereinafter.

BRIEF DESCRIPTION OF THE DRAWINGS

These and other aspects will be apparent from and elucidated with reference to the embodiments described hereinafter. In the following drawings

DETAILED DESCRIPTION

Figure 1:
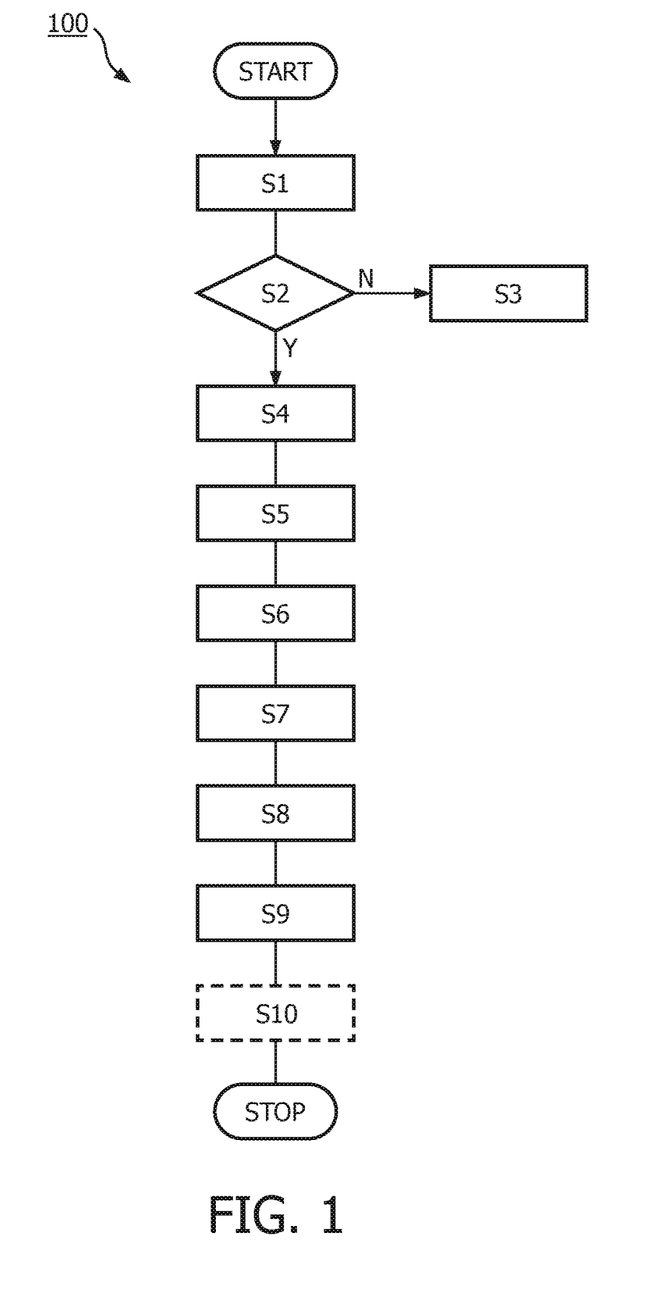
FIG. 1 shows a flow chart of a method for ascertaining a sedentary body posture of a subject according to an embodiment.

FIG. 1 shows a flow chart 100 of a method for ascertaining a sedentary body posture of a subject according to an embodiment. The flowchart 100 has been explained in conjunction with FIGS. 2-5.

Figure 2A:
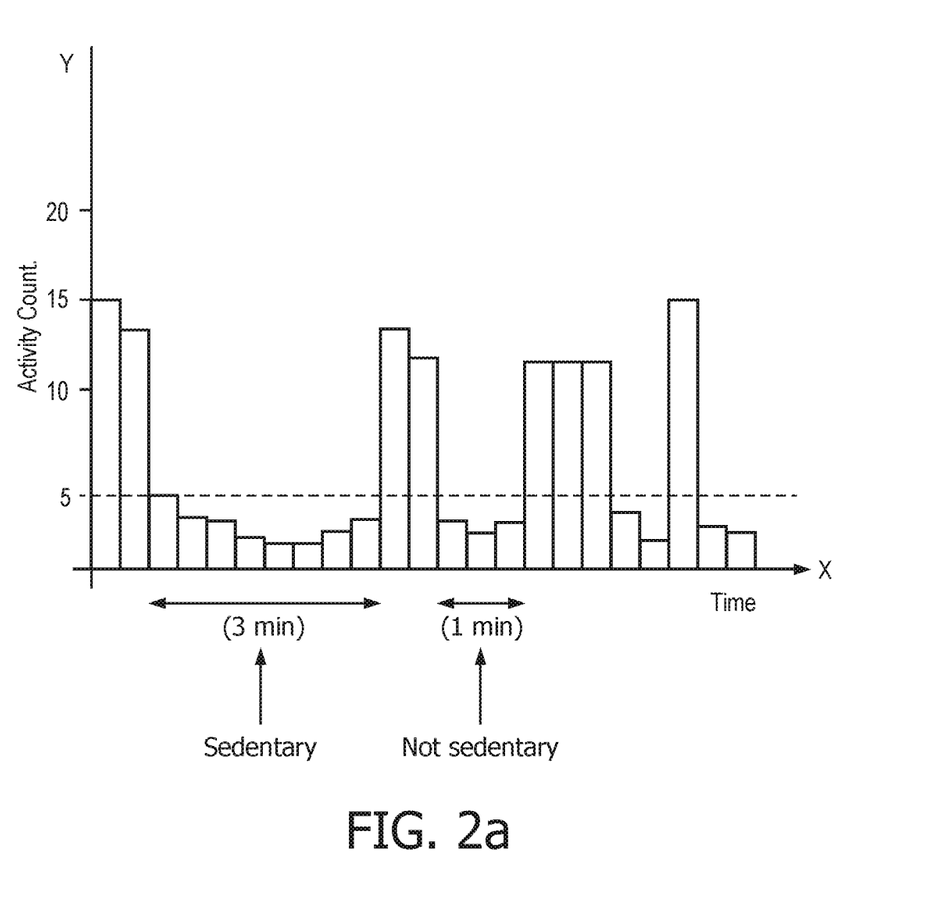
FIG. 2a shows a graph depicting motion information in relation to the time according to the embodiment.

The method begins at S1, wherein accelerometer data is received. The accelerometer data is indicative of motion of the subject. If at S2 the motion information is determined to be above a pre-determined motion threshold then it is understood that the subject is in motion at S3. However, if at S2 the motion information is below the pre-determined motion threshold, then the user is ascertained/classified to be in sedentary state at S4. In an embodiment, the pre-determined motion threshold can be defined as a limit below which if motion information is observed in a motion signal, then the subject is considered to be sedentary and above which the subject is considered to be non-sedentary. Further, in some embodiments, when the motion information is below the pre-determined motion threshold for a pre-defined time interval, the subject is ascertained to be in the sedentary state. As depicted in FIG. 2a, the motion information over time is plotted and the pre-determined motion threshold is set at value 5 for the activity count. In an embodiment, the activity count is a parameter to represent motion information. Thus, if the motion information is determined to be below 5 for the activity count then the subject can be ascertained to be in the sedentary state. However, it has to be understood for the convenience of the user and efficiency of the sedentary state determination, motion information below the pre-determined motion threshold should be considered in combination with the pre-defined time interval/pre-determined time threshold. In this case, it can be clearly seen that if the motion information is below the pre-determined threshold for at least 3 minutes then the person is ascertained to be in the sedentary state, however, if the motion information is below the pre-determined motion threshold but for less than the pre-defined time interval, such as 1 minute, then the person is not ascertained to be in the sedentary state.

In an embodiment, the pre-determined time threshold can be based on a general population data, in which the time threshold is set such that any immediate effects of elevated heart rate, such as after performing an activity are filtered or effects of orthostatic hypotension due to standing up from lying are automatically filtered as elevated heart rate returns to a resting heart rate. It is also termed as recovery time. In other words, the pre-determined time threshold can also be set/chosen based on the recovery time. It is to be noted that the recovery times differ for different people based on various factors, such as age, sex, health status etc. Thus, user-specific characteristics play an important role in understanding/setting of the pre-determined time threshold. Table 1 below provides recovery times related to different users.

TABLE 1

| Type of User | Recovery Time (minutes) |
| --- | --- |
| Young Fit Males | 1.5 |
| Young Unfit Males | 3 |
| Young Fit Females | 2 |
| Young Unfit Females | 5 |
| Old Fit Males | 4 |
| Old Unfit Males | 8 |
| Old Fit Females | 6 |
| Old Unfit Females | 10 |

At S5, once the user is ascertained to be in the sedentary state, the heart rate signal (information) is received. At least one heart rate feature value is derived from the heart rate information at S6. In an embodiment, the heart rate feature is in form of either heart rate (beats per minute) or Inter Beat Intervals (IBIs in ms). In an alternate embodiment, the pre-determined time threshold mentioned above can be also personalized based on the recovery time. Thus, after the heart rate feature, such as heart rate, is received, the method can further wait for heart rate to reach the resting heart rate and then proceed with sedentary posture determination as mentioned below.

The inventors have realized that the mean of IBIs and heart rate are in a particular range for each of the sedentary body postures, namely, sedentarily lying, sedentarily sitting and sedentarily standing. Table 2 below provides the range of mean HR and IBIs for each of the sedentarily body postures. In an embodiment, the mean HR and IBIs for each posture is indicative of an ideal situation of heart, i.e. without any influence of the arousal.

TABLE 2

|  | Lying | Sitting | Standing |
| --- | --- | --- | --- |
| Mean HR (bpm) | <62 bpm | 62-73 bpm | >73 bpm |
| Mean IBI (ms) | >968 ms | 822-968 ms | <822 ms |

Table 2 provides the pre-determined range for each sedentary posture of heart rate and IBIs that is indicative of general population data. Such population data can be gathered for various heart rate features. In an alternate embodiment, the ranges above can also be calibrated during a calibration phase for the user. For instance, a protocol can be followed by the user, in which, the user can be asked to be in different sedentary body postures and accordingly the corresponding heart rate feature range for each posture for the user can be stored in the table. Thereafter, the calibrated ranges can be used for determining sedentary postures. This is in particular advantageous when the user is suffering from a chronic heart disease because of which his heart rate/IBI does not fall in or follow a typical population data. Few examples of such heart diseases could be bradycardia, tachycardia, atrial fibrillation, etc. Similarly, such ranges for different heart rate features can be accordingly understood and stored in form of tables and be used for ascertaining sedentary body postures.

Figure 2B:
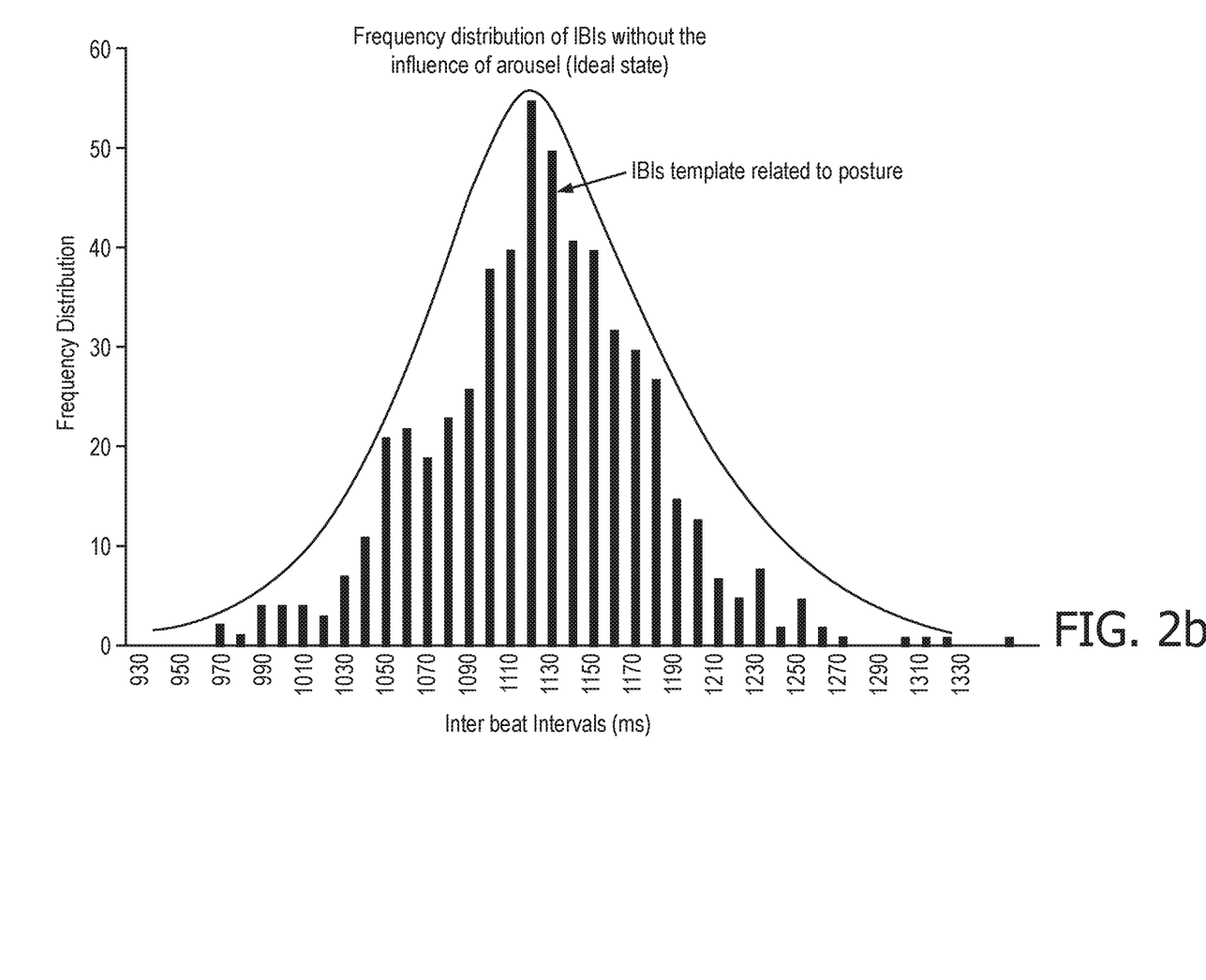
FIG. 2b shows a Gaussian frequency distribution of a heart rate feature, i.e. Inter beat Intervals, for sedentarily lying in an ideal state, i.e. without the influence of arousal, according to the embodiment.

In another embodiment the frequency distribution of IBIs can be stored for each of the sedentary body posture. It is understood by the inventors that frequency distribution of the IBIs follows a Gaussian frequency distribution. An example of frequency distribution of IBIs for sedentarily lying is shown in FIG. 2b. Such template also be pre-stored as a baseline distribution which can be later used for ascertaining the sedentary body posture.

At S7, influence of arousal is removed/filtered from the derived heart rate feature value. It may be appreciated by a person skilled in the art that when the person is sedentary, there are instances when he may be thinking, tensed, etc. which invariably increases the cognitive load or stress on the subject. In such instances, the arousal increases the heart rate or in other words it decreases the mean IBIs. Thus, it may be advantageous to remove effect of the arousal from the derived heart rate feature value before ascertaining sedentary body posture. There are various ways to remove arousal from the heart rate signal.

In an embodiment, influence of arousal is removed based on the skin conductance measured during the person is sedentary to further determine one of the sedentary body postures. It is well known in the art already that influence of arousal can be seen in skin conductance of the subject. For instance, in an example depicted in FIG. 3, the subject is sedentary and in a point in time (at t10) a loud noise is introduced. It can be seen that influence of arousal, such as of a loud noise, is seen in the heart rate signal and skin conductance signal between t10-t12. For rest of the time, i.e. t1-t10, both the signals were rather constant without any spikes.

Figure 3:
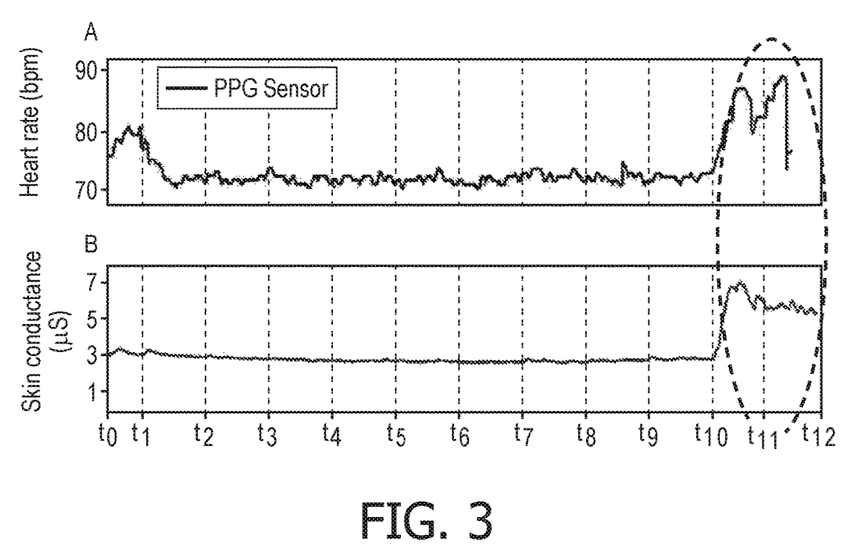
FIG. 3 shows impact of arousal component on a heart rate feature and skin conductance according to an embodiment.
Figure 4:
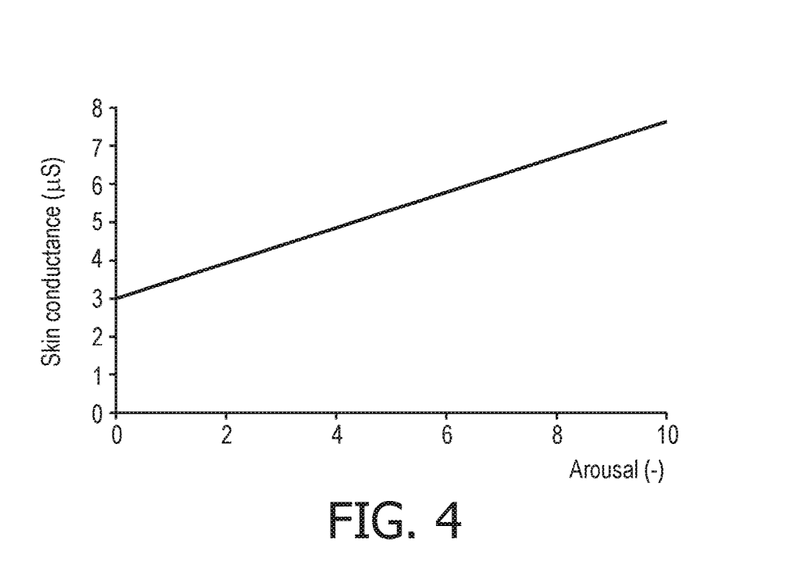
FIG. 4 shows relation between skin conductance and arousal according to the embodiment.

Removal of arousal component from the heart rate information based on the skin conductance is further explained with the help of the above example. In the current embodiment, the relation between arousal and skin conductance (SC) can be plotted in linear fashion. Thus, the relation between arousal and skin conductance mathematically can be expressed as $$SC = \alpha_1 + \alpha_2 \, \text{Arousal} \quad (1)$$

where SC is average skin conductance value during the arousal moment. In this case SC=6 µS based on FIG. 3 (arousal depicted in the dotted lines); and $\alpha_1$ and $\alpha_2$ are pre-defined constants. In the current example, $\alpha_1$=3 µS and $\alpha_2$=0.5 Thus, based on (1) Arousal can be calculated as 6. The relation between arousal and skin conductance is further plotted in FIG. 4.

Further, heart rate value attributing solely due to the influence of arousal, also can be referred to as arousal value, can be expressed mathematically as $$(HR_{Arousal}) = \beta \cdot \text{Arousal} \quad (2)$$

In the current formula $\beta$=2.5 is a constant, thus, based on the calculated arousal from (1), $HR_{Arousal}$ is calculated based on (2) as 15 bpm. In other words heart rate indicative of arousal is 15 bpm.

Furthermore, in the current example, $HR_{total}$ is the heart rate information including arousal, which can be further expressed as:

$$HR_{total} = HR_{sedental} + HR_{Arousal} \quad (3)$$

Thus, if the incoming mean heart rate information, i.e. from t0-t12, is 87 bpm, the $HR_{sedentary}$ (Heart rate indicative of sedentary body posture) based on (3) is 72 bpm.

After the heart rate feature value ($HR_{sedentary}$), in this case the heart rate, is determined, it is compared with the pre-defined ranges provided in Table 1 for the different sedentary body postures at S8. The comparison leads to ascertaining sedentary body posture as "sedentary sitting" at S9. The subject may then be alerted to change the posture or take a break at S10.

In another embodiment, unlike the linear relation expressed above, the relation between arousal and skin conductance; and between arousal and heart rate features can be expressed in more complex mathematical models.

Figure 5A:
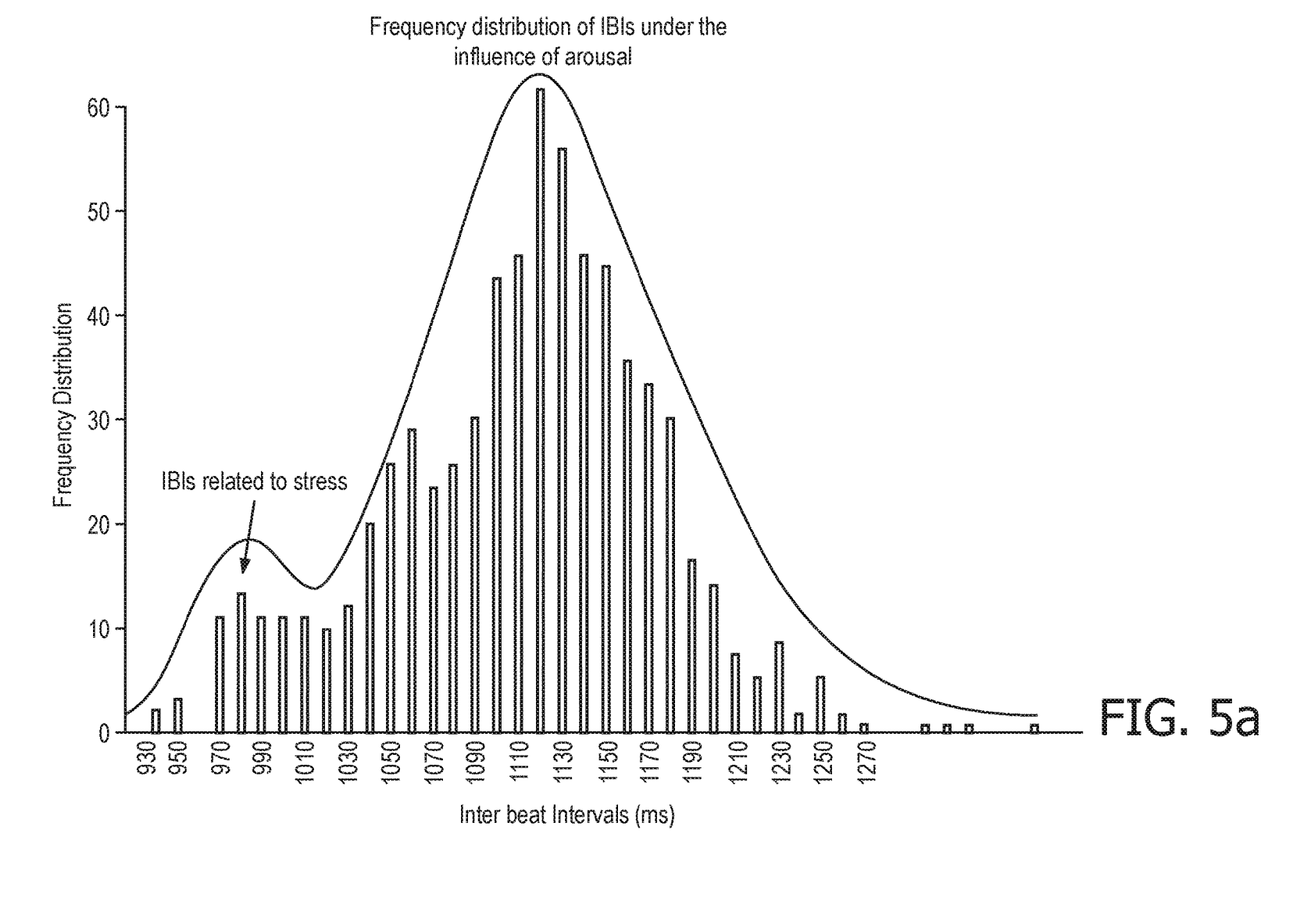
FIG. 5a shows a frequency distribution of the IBIs in a sedentary body posture along with arousal according to another embodiment.
Figure 5B:
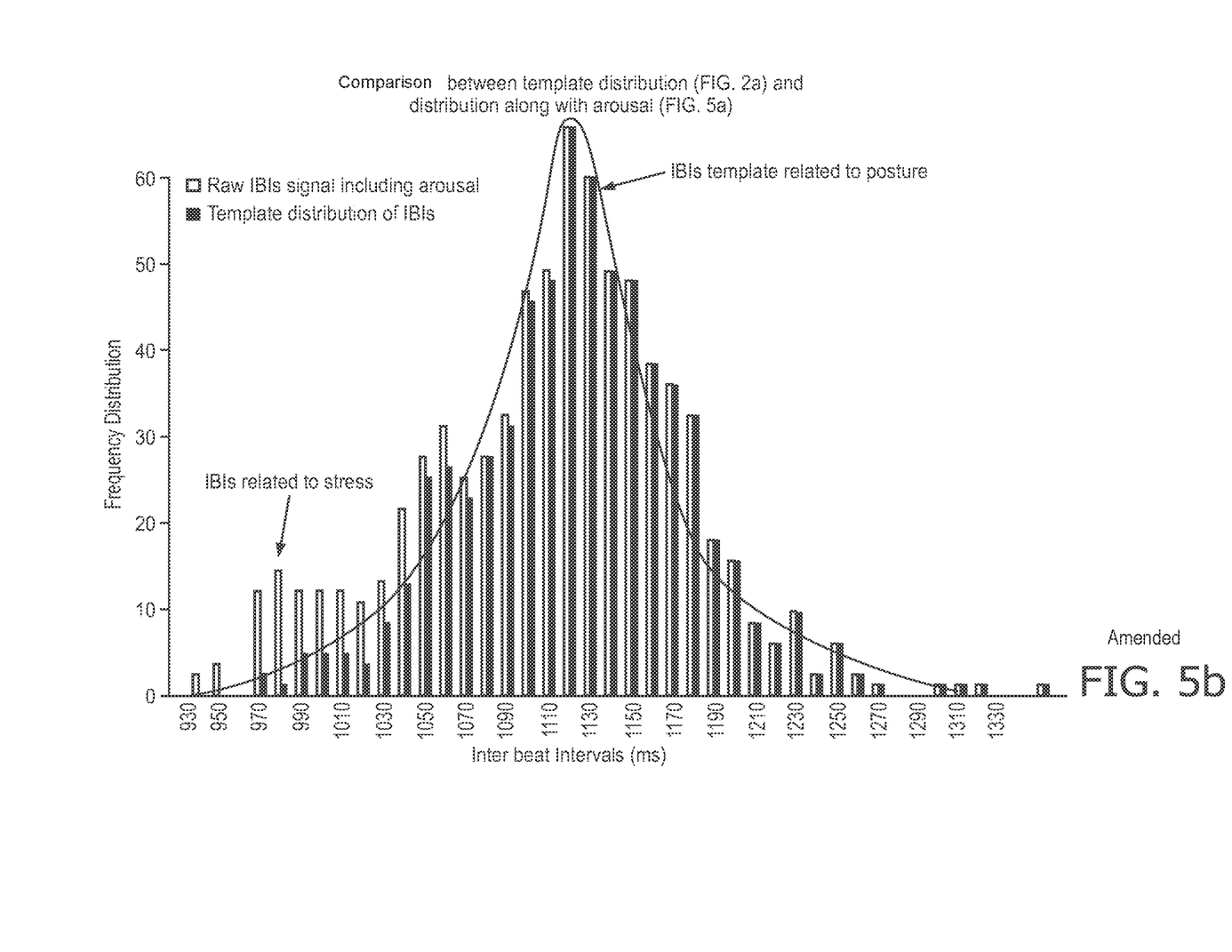
FIG. 5b shows a comparison between the frequency distribution of IBIs without the influence of arousal and the frequency distribution of IBIs with the influence of arousal according to another embodiment.

Another way of removing influence of arousal from the heart rate feature is described below. In the current example, the heart rate feature is IBIs. As explained above, inventors have realized that the IBIs follow a typical Gaussian Frequency Distribution (FIG. 2*b*). Thus, if the person is ascertained to be sedentary at S4, the IBIs associated with the heart rate information received at S5 are derived at S6 and constantly plotted as frequency distribution for a pre-defined recording time. In an embodiment, the pre-defined recording time is 5 minutes. The pre-defined recording time is based on the insight that data gathered in this time must be sufficient for analysis of posture determination. The inventors have found that typically five minutes is a good indication for gathering heart rate features. An exemplary plotting of IBIs derived at S6 is depicted in FIG. 5*a*. Thereafter to determine the sedentary body posture, it is checked if it matches the template Gaussian distribution, such as depicted in FIG. 2*b*. However, given that the person is under the influence of arousal, the frequency distribution will change shape from a normal Gaussian distribution (FIG. 2*b*) to a bi-modal skewed distribution (as depicted in FIG. 5*a*).

Since it is understood that the highest IBIs (lowest HR), i.e. most frequent IBI, is related to the posture (in the example, between 1120 ms and 1130 ms, the bigger curve on the right (FIG. 5*a*) will be associated to the current posture, whereas the IBIs values forming the left curve will be associated to arousal and not to posture. In an embodiment, the association of the bigger curve to the sedentary posture is based on the percentage of frequency distribution in the pre-defined IBI range. In this case, it is evident that majority of the range is in the "Lying" posture. Thus, the comparison, depicted in FIG. 5*b*, between the bi-modal skewed distribution and the template Gaussian distribution for "Lying" will filter/remove the IBIs arising from the arousal. These filtered values will provide mean IBIs ascribable solely to posture. In this example:

Mean IBIs before filtering 967 ms (i.e. based on FIG. 5*a*)
Mean IBIs after filtering 980 ms Thus, the means IBIs after filtering, i.e. removing the arousal value (in this case 980−967=23 ms), is indicative of the current sedentary body posture. It is understood that a person skilled in the art is aware of comparing such frequency distribution curves to isolate the outliers (in this case the arousal component). One of the ways used in statistical analysis is called curve fitting.

At S8, 980 ms is looked up in the table 1 and it is ascertained that the body posture is "lying down" at S9. It can be seen that if the mean IBIs were not filtered by removing the means IBIs resulting from the arousal, then the sedentary posture would have been misclassified as "sedentary sitting". The term 'filtering' in the current embodiment means to compensate/adjust the mean IBIs information by removing the effect of the arousal effect on IBI.

In an alternate embodiment, instead of calculating mean IBIs, the two frequency distributions, i.e. template (FIG. 2*b*) and bimodal skewed (FIG. 5*a*), can be simply compared to filter the arousal component to arrive at the template distribution which can then be used to ascertain the sedentary body posture. Optionally, the person may be alerted at S10 based on the sedentary body posture. For instance, the person has been asked not to lie down for more than a few minutes in the day by a doctor. In such as case, if he is determined to sedentarily lying and further if he is lying for more than pre-determined sedentary time threshold, he may be alerted accordingly. It may be appreciated by a person skilled in the art, if the person (user/subject) becomes non-sedentary, the method steps described above will start again, once the person is ascertained to be in a sedentary state. In various embodiments, once the sedentary body posture is determined based on the gathered heart rate feature data in the pre-defined recording time, the alerting can be postponed, when the person continues to be in sedentary state (i.e. motion less than the pre-determined motion threshold), till the pre-determined sedentary time threshold has elapsed. This helps in power management as continuous heart rate data is not required anymore. However, if the person becomes non-sedentary after the determination of the sedentary body posture, the method steps described above will start again, once he is ascertained to be in the sedentary state again.

In a further embodiment, an additional step of filtering may be performed for specific cases of arrhythmias, such as atrial fibrillation. If irregular heartbeat events are recorded in the pre-defined recording time for majority of the time, for instance, for a patient suffering from atrial fibrillation can have multiple events because of which heart beats deviate from the calibrated range/population data of heart beat ranges, then the method will not use the gathered IBIs to determine the sedentary body posture but will wait till the event subsides. For instance, a Poincare plot can be used to understand if the IBIs gathered in the pre-defined recording time indicates multiple events of atrial fibrillation. Poincare plots are well known from the literature to indicate arrhythmia. Furthermore, if the plot does not indicate arrhythmias, atrial fibrillation for the majority part of the gathered IBIs, then the filtering can be performed based on the method steps described above in conjunction with the arousal removal. This is because, a one-time or minor event in the pre-defined recording time will lead to bi-modal distribution, which can be then filtered based on the most frequent IBI, which will indicate the posture and thus the IBIs not related to the posture, will be filtered from the bi-modal distribution to determine the sedentary posture. It may be appreciated that if such an event of atrial fibrillation overlaps with arousal event then the IBIs will be filtered together because it will lead to a bimodal distribution again. Thus to summarize, the method further filters arrhythmias, such as tachycardia, bradycardia, atrial fibrillation, that are not chronic in nature and occur in the pre-defined recording time.

Figure 6:
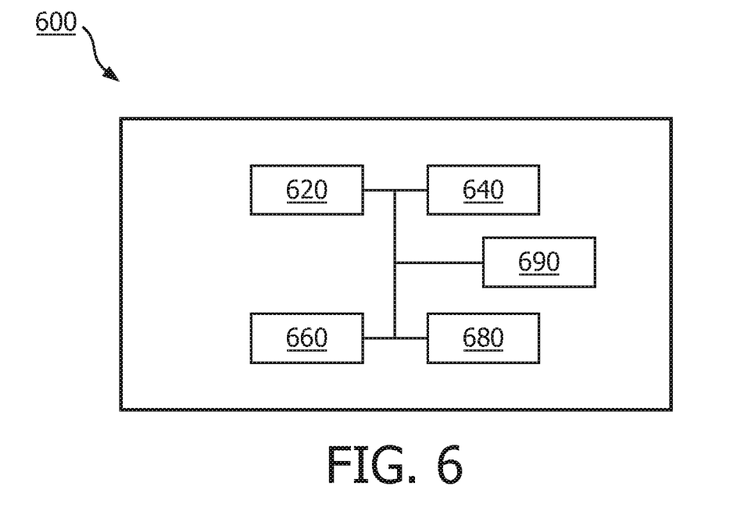
FIG. 6 shows a system including a device according to an embodiment.

FIG. 6 shows a schematic diagram of an embodiment of a system 600 for ascertaining a sedentary body posture of a subject. The system 600 includes an accelerometer 620 for acquiring motion information of the subject. Such accelerometers are generally known in the art. They can be worn e.g. around the leg or the arm, for instance a wrist worn device like a watch or at the ankle, but may also be mounted to any other part of the body. The accelerometer 620 generally provides three-dimensional accelerometer data, i.e. a separate accelerometer signal for each of three orthogonal directions indication the acceleration in the respective direction. However, various embodiments also work with other accelerometer data, e.g. a single accelerometer signal (i.e. one-dimensional accelerometer data) or two-dimensional accelerometer data, as long as the desired motion information in some way reflected in the accelerometer data.

The system 600 also includes a heart rate (HR) sensor 640 to obtain heart rate signal indicative of heart rate the subject. In an embodiment, the HR sensor 640 is a Photoplethysmogram (PPG) sensor. Various other HR sensors, such as ECG sensor, bio-impedance, galvanic skin response and other surface electrical recordings on the body may be used to obtain the HR signal of the subject.

The system 600 further includes a device 660 for ascertaining a sedentary body posture of a subject based on the motion information captured by accelerometer 620. The device 660 may be implemented in hardware and/or software. E.g. a processor or computer may be configured accordingly to implement the elements of the device 660 as explained below. As will be understood, the term "processor" will be understood to encompass various hardware such as microprocessors, field programmable gate arrays (FPGAs), application-specific integrated circuits (ASICs), or other similar hardware capable of performing various functionality described herein. In some embodiments, the processor may perform such functionality by executing instructions stored in memory or by operating on data stored in memory. As used herein, the term "memory" will be understood to encompass various types of memories such as L1/L2/L3 memory, system memory, or storage. Further, as used herein, the term "non-transitory computer-readable medium" and similar terms will be understood to encompass both volatile memories (e.g., SRAM and DRAM) and non-volatile memories (e.g., flash, magnetic, and optical memories) but to exclude transitory signals.

The system 600 further includes an output interface 680 for outputting the sedentary body posture. The output interface 680 may be a display for displaying the sedentary body posture, but may also be a transmitter for transmitting the determined sedentary body posture to another device, e.g. a smartphone, computer or website, for further processing (e.g. for medical purposes or storage in a health record) and/or display there.

The system 600 furthermore optionally includes a Galvanic Skin Response (GSR) sensor 690. SR sensor 690 provides a signal indicative of skin response, which is specifically useful in discerning events of arousal, such as stress, excitement, etc.

All elements of the system 600 may be integrated into a common wearable device (as shown below in more detail for another embodiment of the system) or may be implemented as separate devices. For instance, only the accelerometer 620 and HR sensor 640 are mounted to the subject's body and transmits the accelerometer data and the heart rate signal data (in real time in a wired or wireless manner) to the device 660 for processing. The device 660 may be configured as or part of a computer, laptop, smartphone, tablet or any other device that is configured for carrying out the steps performed by the device 660.

Figure 7:
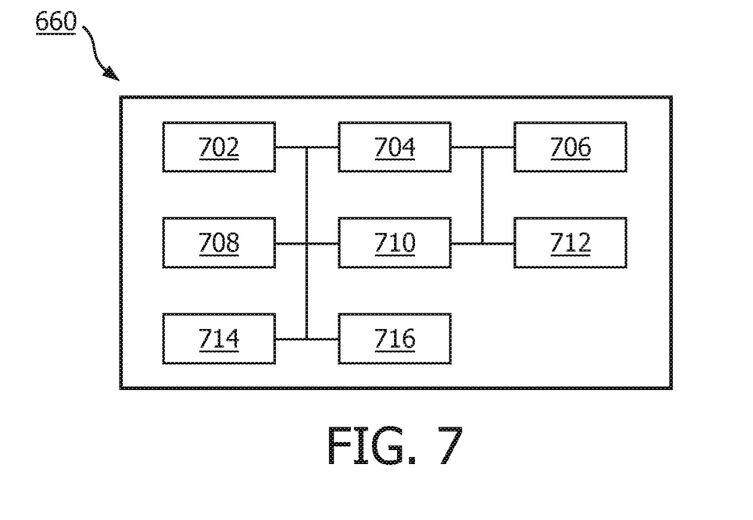
FIG. 7 shows the device ascertaining a sedentary body posture of a subject according to an embodiment.

FIG. 7 shows a schematic diagram of an embodiment of device 660 according to various embodiments for ascertaining the body posture of the subject. To implement the above-described method, the device 660 includes a sedentary state determination unit 702, an input unit 704, a heart rate feature unit 706, a storage unit 708, a sedentary posture determining unit 710, an arousal determination unit 712, an alert unit 714 and a calibration unit 716.

The sedentary state determination unit (SSDU) 702 receives motion information from the accelerometer 620. The SSDU 702 further checks if the motion information is indicative of the sedentary state. As described above, the sedentary state can be described as when there are no spikes observed in the motion signal for a pre-defined amount of time. Such a signal is indicative of sedentary state of the subject. In an embodiment, SSDU 702 determines the sedentary state by checking if the motion information corresponding to the subject is below a pre-determined threshold motion information. SSDU 702 determines the sedentary state as explained in the steps S2 and S4 of the FIG. 2.

After, it is established that the subject is in the sedentary state, the input unit 704 further receives the HR signal from the HR sensor 640. As described above, the heart rate signal indicative of at least one heart rate feature. Thereafter, the heart rate feature unit (HRFU) 706 derives a heart rate feature value, from the obtained heart rate signal, corresponding to at least one heart rate feature. One of the examples of heart rate feature is heart rate typically expressed in Beats per minute (bpm). Other example of the heart rate feature is Inter Beat Intervals, typically expressed in milli seconds (ms). Thus, an example of heart rate feature value for heart rate is 87 bpm. Similarly, an example of heart rate feature value for mean IBIs is 980 ms.

The sedentary body posture determination unit (SDPDU) 710 determines the sedentary body posture of the subject based on comparison between the derived heart rate feature value and stored ranges for each of the body postures to determine the sedentary body posture. The ranges are stored in a storage unit 708. The ranges are stored in form of a table, such as Table 2, and/or Gaussian frequency distribution (also depicted in FIG. 2b) of the at least one heart rate feature. In addition to table 2, table 1 discussed above is also stored in the storage unit 708. An example of the storage unit 708 can be a semiconductor memory element.

In an embodiment, the arousal unit 712 filters the arousal value/component from the heart rate signal to determine the heart rate feature value indicative of heart rate feature without the influence of arousal. Such a heart rate feature value, i.e. without the arousal, is used for comparison with the ranges stored in the storage unit 708. In an embodiment, the arousal determination unit 712 interacts/communicates with the HR sensor 640 and the GSR sensor 690 to determine the arousal value. In other embodiment, the arousal determination unit 712 interacts/communicates with HR sensor 640 only to determine the arousal value. The arousal determination unit 712 executes one or more combination of the methodologies (S7) as described in FIG. 1. Once the sedentary posture is ascertained, the alert unit 714 provides an alert signal to the user if the user continues to be in the sedentary posture for more than a pre-defined sedentary time threshold.

In a further embodiment, the calibration unit 716 further calibrates the stored ranges for each of the sedentary body postures. For example, the SSPDU 710 may prompt the user via the output interface 660 to confirm the determined sedentary body posture, such as "Sedentary Lying". However, if the subject disagrees with the determination and suggests the state is "Sedentary Sitting", then the stored range corresponding to the "Sedentary Lying" can be mapped to "Sedentary sitting". Similarly, the range corresponding to "Sedentary Sitting" will be mapped to "Sedentary Standing". A new range can be calculated for "Sedentary Lying" based on the "Sedentary Sitting". For instance, the calibration unit 716 may use a pre-determined margin to calculate the range for "Sedentary Lying" based on "Sedentary Sitting".

In another embodiment, the calibration unit 716 may provide one or more instructions to the subject via the output interface 660. For instance, the output interface 660 provides an instruction, such as "Sit Still for 2 minutes". Thereafter, the range of heart rate feature, such as range of heart rate (bpm) will be stored in the table, such as Table 1, for determination of sedentary state body posture for later point in time. Similarly, range corresponding to different heart rate features can be stored in a table for later use. Of course, the Gaussian frequency distribution can also be stored in the storage unit 708 for each body posture by the calibration unit 716.

Figure 8:
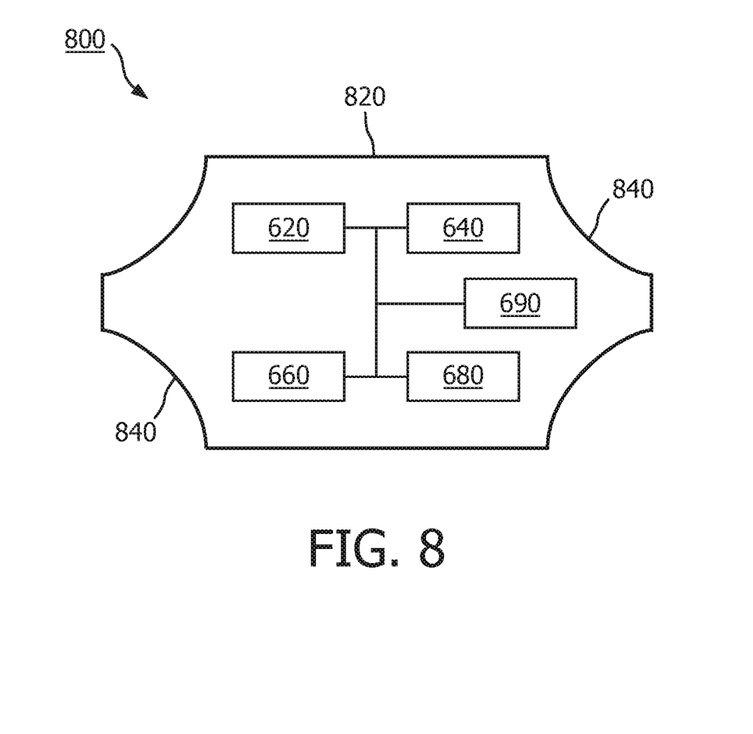
FIG. 8 shows a system including the device according to another embodiment.

FIG. 8 shows a schematic diagram of another embodiment of a system 800. In the current embodiment a housing 820 is provided for housing the accelerometer 620, the HR sensor 640, the device 660 and the output interface 680 to integrate all elements as an integrated wearable device. Further, a holding element 840, such as a belt or wrist band, is provided for holding the housing at a body part of the subject. The system 800 may further optionally include the GSR sensor 690.

While various embodiments have been illustrated and described in detail in the drawings and foregoing description, such illustration and description are to be considered illustrative or exemplary and not restrictive; the advna is not limited to the disclosed embodiments. Other variations to the disclosed embodiments can be understood and effected by those skilled in the art in practicing the techniques and concepts described herein, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A method of ascertaining a sedentary body posture of a subject, the method comprising:
   in a processor:
   determining if the subject is in a sedentary state, wherein the subject is determined to be in the sedentary state when the subject is being sedentary for at least a predetermined time threshold;
   receiving a heart rate signal indicative of at least one heart rate feature of the subject;
   deriving, from the received heart rate signal, at least one heart rate feature value corresponding to the at least one heart rate feature, when the subject is determined to be in the sedentary state, wherein deriving the heart rate feature value further comprises filtering an arousal value from the received heart rate signal, so as to reduce an influence of the arousal on the determination of the sedentary posture; and
   determining the sedentary body posture of the subject based on a comparison between the derived at least one heart rate feature value and a pre-determined range associated with the corresponding at least one heart rate feature, wherein for each sedentary body posture the pre-determined range corresponding to the at least one heart feature is stored.

2. The method according to claim 1, wherein filtering the arousal value further comprises:
   receiving Inter-Beat-Intervals for a pre-defined recording time, wherein the Inter-Beat-Intervals is a heart rate feature;
   plotting a frequency distribution of the Inter-Beat-Intervals gathered in the predefined recording time; and
   comparing the plotted frequency distribution in the pre-defined recording time with a template frequency distribution associated with Inter-Beat-Intervals for different sedentary body postures.

3. The method according to claim 2, wherein the comparing step further comprises comparing a mean Inter-Beat-Intervals associated with the plotted frequency distribution in the pre-defined recording time and a mean Inter-Beat-Intervals associated with the template frequency distribution, wherein comparing the mean Inter-Beat-Intervals determines the sedentary body posture.

4. The method according to claim 1, wherein filtering the arousal value further comprises calculating a heart rate ($HR_{Arousal}$) indicative of arousal based on Galvanic Skin Response (GSR) signal and removing the calculated heart rate ($HR_{Arousal}$) indicative of arousal from an overall heart rate ($HR_{Total}$) received from the heart rate signal to derive a heart rate ($HR_{Sedentary}$) indicative of the sedentary body posture.

5. The method according to claim 1, wherein determining if the subject is sedentary further comprises checking if a motion information corresponding to the subject is below a pre-determined motion threshold.

6. The method according to claim 1, wherein the predetermined range corresponding to each sedentary body posture is stored in at least one of: a table and in form of a Gaussian distribution for a pre-defined time interval.

7. The method according to claim 1, further comprising calibrating the pre-determined range corresponding to the at least one heart rate feature for the sedentary posture.

8. The method according to claim 7, wherein calibrating the pre-determined range further comprises:
providing one or more instructions to the subject to bring the subject to the sedentary body posture; and
recording a new range corresponding to at least one heart rate feature associated with the sedentary body posture, wherein the recorded new range is stored as the pre-determined range corresponding to the at least one heart rate feature associated with the sedentary body posture.

9. The method according to claim 1, further comprising alerting the subject if the subject is determined to be in the sedentary body posture for a time period greater than a pre-defined sedentary time threshold.

10. A device for ascertaining a sedentary body posture of a subject, the device comprising:
a sedentary state determination unit configured to check if the subject is in a sedentary state, wherein the subject is determined to be in the sedentary state when the subject is being sedentary for at least a pre-determined time threshold;
an input unit for obtaining a heart rate signal indicative of at least one heart rate feature of the subject;
a heart rate feature unit for deriving, from the obtained heart rate signal, a heart rate feature value corresponding to the at least one heart rate feature, when the subject is in the sedentary state, wherein the heart rate feature unit further comprising an arousal determination unit for filtering an arousal value from the received heart rate signal, so as to reduce an influence of the arousal on the determination of the sedentary posture;
a storage unit for storing pre-determined ranges of the heart rate feature values for each of a plurality of the sedentary body postures; and
a sedentary body posture determination unit for determining the sedentary body posture of the subject based on a comparison between the derived heart rate feature value and the stored ranges.

11. The device according to claim 10, wherein the sedentary state determination unit is arranged to determine the sedentary state by checking if a motion information corresponding to the subject is below a predetermined motion threshold.

12. The device according to claim 10, further comprising a calibration unit for calibrating the pre-determined range corresponding to the at least one heart rate feature for each of the sedentary posture.

13. The device according to claim 12, wherein the calibration unit is further arranged to:
provide one or more instructions to the subject to bring the subject to the sedentary body posture;
record a new range corresponding to the heart rate feature associated with the sedentary body posture; and
store the recorded new range as the pre-determined range corresponding to the at least one heart rate feature associated with the sedentary body posture in the storage unit.

14. The device according to claim 10, further comprising an alert unit to alert the subject if the subject is determined to be in the sedentary body posture for a time period greater than a pre-defined time threshold.

* * * * *